United States Patent [19]

Spang et al.

[11] Patent Number: 5,047,571

[45] Date of Patent: Sep. 10, 1991

[54] PROCESS FOR THE PREPARATION OF 2-CYANO-3,3-DIARYLACRYLATES

[75] Inventors: Peter Spang, Ingbert; Peter Neumann, Mannheim, both of Fed. Rep. of Germany

[73] Assignee: BASF Aktiengesellschaft, Ludwigshafen, Fed. Rep. of Germany

[21] Appl. No.: 508,689

[22] Filed: Apr. 13, 1990

[30] Foreign Application Priority Data

Apr. 29, 1989 [DE] Fed. Rep. of Germany ....... 3914382

[51] Int. Cl.$^5$ .......................................... C07C 253/30
[52] U.S. Cl. .................................... 558/402
[58] Field of Search ................................ 558/348, 402

[56] References Cited

U.S. PATENT DOCUMENTS

| | | | |
|---|---|---|---|
| 2,822,348 | 2/1958 | Haslam | 560/92 X |
| 2,947,729 | 8/1960 | Sullivan | 560/92 X |
| 3,057,828 | 10/1962 | McNeil, Jr. | 560/92 X |
| 3,149,148 | 9/1964 | Kladko et al. | 260/465 |
| 3,215,724 | 11/1965 | Strobel et al. | 260/465 |
| 4,002,667 | 1/1977 | Thompson | 560/92 |
| 4,289,895 | 9/1981 | Burkhardt et al. | 560/92 |

OTHER PUBLICATIONS

Hilgetag et al., Weygand Hilgetag Preparative Organic Chemistry, (1972), pp. 375–376, John Wiley & Sons.

*Primary Examiner*—Joseph Paul Brust
*Attorney, Agent, or Firm*—Oblon, Spivak, McClelland, Maier & Neustadt

[57] ABSTRACT

The preparation of 2-cyano-3,3-diarylacrylates I

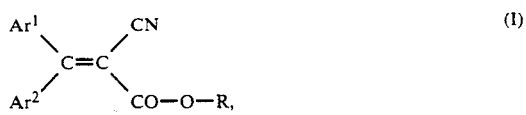

(in which $Ar^1$ and $Ar^2$ are aromatic radicals and R is an aliphatic radical having from 3 to 30 carbon atoms) by reacting a 2-cyano-3,3-diarylacrylate II

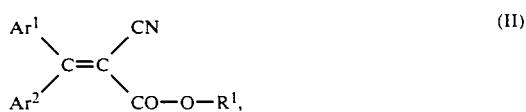

(in which $R^1$ is methyl or ethyl) with an alcohol III

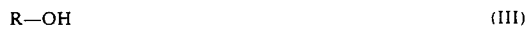

in the presence of a basic catalyst with removal of the alcohol $R^1$-OH formed.

The esters of formula I are valuable UV absorbing agents for, say, plastics materials.

4 Claims, No Drawings

PROCESS FOR THE PREPARATION OF 2-CYANO-3,3-DIARYLACRYLATES

The present invention relates to a novel process for the preparation of 2-cyano-3,3-diaryl acrylates of the general formula I:

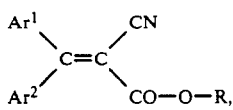

in which $Ar^1$ and $Ar^2$ are aromatic radicals and R is an aliphatic radical having more than 2 carbon atoms.

It is generally known (cf. U.S. Pat. No. 3,215,724 for example) that the compounds of formula I, which are suitable for use as UV absorbers in organic substances, can be prepared by reacting a diaryl ketone with a cyanoacetic ester according to the following reaction scheme:

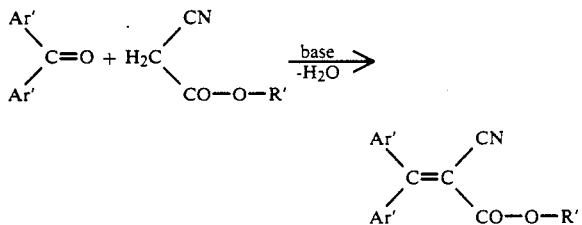

(Ar'=aryl; R'=an organic radical).

However, this procedure suffers from the drawback that the product is usually discolored and purification thereof is extremely laborious.

Thus it is an object of the present invention to overcome said drawback.

Accordingly, we have found a process for the preparation of a 2-cyano-3,3-diarylacrylate of formula I, which is characterized in that a 2-cyano-3,3-diarylacrylate of the general formula II below

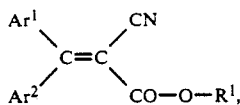

in which $R^1$ stands for methyl or ethyl, is reacted with an alcohol of formula III:

in the presence of a basic catalyst with continuous removal of the resulting alcohol $R^1$-OH.

The methyl or ethyl 2-cyano-3,3-diarylacrylate II serving as starting material is known per se or can be prepared in a pure form by known methods by reacting a benzophenone component with an activated cyanoacetic ester (cf. U.S. Pat. No. 3,149,148 for example).

With a view to the desired properties of the UV absorbers I to be prepared, the starting materials II are preferably those in which $Ar^1$ and $Ar^2$ have the following meanings:

isocyclic unsubstituted aryl such as α- and β-naphthyl and, in particular, phenyl;

substituted aryl, in particular substituted phenyl having preferably up to 3 substituents selected from the following:

$C_1$-$C_{18}$-alkyl, particularly methyl or ethyl, $C_1$-$C_{18}$-alkoxy, particularly methoxy, halogen, preferably chlorine, a radical containing aryl, preferably benzyl, ethylbenayl or phenoxy, a nitrogen-containing group, preferably cyano.

The radicals R in the target compounds of the invention are preferably $C_4$-$C_{18}$-alkyl, in particular 2-ethylhexyl or n-octyl, and $C_4$-$C_{18}$-mono- or poly-alkoxyalkyl, preferably ethoxyethyl or $CH_3$—O—$CH_2CH_2$—O—$CH_2CH_2$.

The radicals R may themselves carry further substituents such as aryl, cyano, tertiary amino, halogen, carbonyl and aldehyde groups.

Suitable catalysts for the transesterification are basic alkali metal salts and alkaline earth salts, preferably those which are insoluble in both the educts and the products and can be readily isolated on termination of the reaction, particularly preferred salts being the carbonates of sodium, potassium or calcium and sodium bicarbonate;

alkaline earth oxides, preferably calcium or magnesium oxide, and basic zeolites.

The amount of catalyst used is generally from 1 to 80% and preferably from 5 to 50% molar of the amount of ester II used.

The amount of alcohol III must be at least equimolar to the amount of 2-cyano-3,3-diarylacrylate II used. We prefer to use amounts ranging from 200 to 500% molar of alcohol.

The alcohol $R^1$—OH formed is removed by distillation, preferably assisted by a stream of an inert gas such as, preferably, argon or nitrogen. The preferred rate of flow of said inert gas is from 20 to 80 liters/hour.

It is preferred to operate at a temperature of from 90° to 180° C. and in particular from 120° to 160° C.

Special pressure conditions are not required, and the reaction is generally carried out at atmospheric pressure.

Suitable solvents are inert higher-boiling compounds such as xylenes, but use may also be made of toluene or a mixture of the alcohol R—OH used with a liquid, short-chain alkane such as hexane or heptane. It is preferred to carry out the reaction in the alcohol R—OH without any additional solvent.

The process of the invention may be carried out continuously or batchwise. When using a continuous procedure, the reactants are preferably passed through a fixed bed of an insoluble base.

The reaction mixture is worked up in conventional manner so that a detailed description of this procedure is unnecessary.

The target products I are obtained in a high state of purity and in almost quantitative yield and show no discoloration.

EXAMPLE 1

Preparation of 2-ethylhexyl 2-cyano-3,3-diphenylacrylate

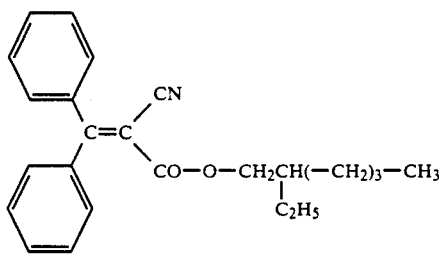

138.5 g (0.5 mole) of ethyl 2-cyano-3,3-diphenylacrylate and 196 g (1.5 mole) of 2-ethylhexanol were caused to react at 130° C. in the presence of 5 g (0.05 mole) of sodium carbonate, the ethanol formed being removed by distillation assisted by a stream of nitrogen (approx. 22 l/h). The transesterification reaction was complete after about one hour, and the solution was filtered from the sodium carbonate while still hot. The purity of the thus obtained 2-ethylhexyl 2-cyano-3,3-diphenylacrylate was already very high at this stage.

Purification by film evaporation provided the ester in the form of a light-yellow oil in 97% yield and having a purity of 99.8% as determined by gas-chromatographic analysis.

The same results were obtained using, as base, calcium carbonate or magnesium oxide for a reaction period of from 2 to 3 hours.

EXAMPLE 2

Preparation of octyl 2-cyano-3,3-diphenylacrylate

This compound was prepared in a yield of 96% in a manner similar to that described in Example 1 and comprised a light-yellow oil.

EXAMPLE 3

Preparation of isodecyl 2-cyano-3,3-diphenylacrylate

In a manner similar to that described in Example 1, a mixture of primary isodecanols was converted to the corresponding ester mixture obtained as a light-yellow oil. The yield was 88%.

We claim:

1. A process for the preparation of a 2-cyano-3,3-diarylacrylate of the general formula I

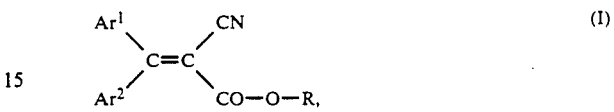

in which $Ar^1$ and $Ar^2$ each denote phenyl and R is an aliphatic radical of from 3 to 30 carbon atoms, wherein a 2-cyano-3,3-diarylacrylate of the general formula II

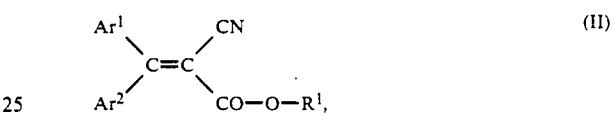

in which $R^1$ stands for methyl or ethyl, is reacted with an alcohol of formula III $$R-OH \qquad (III)$$

in the presence of a basic catalyst, selected from the group of basic alkali metal salts and alkaline earth salts, alkaline earth oxides and basic zeolites, at a temperature of from 90° to 180° C., with continuous removal of the resulting alcohol R'—OH, wherein the continuous removal of the alcohol R'OH is effected with a stream of inert gas.

2. A process as claimed in claim 1 in which R denotes $C_8$-$C_{12}$-alkyl.

3. A process as claimed in claim 2 carried out at atmospheric pressure.

4. A process as claimed in claim 3 wherein the amount of alcohol of formula (III) is 200 to 500% of the amount of the compound of formula (II).

* * * * *